(12) United States Patent
Jia et al.

(10) Patent No.: US 9,120,040 B2
(45) Date of Patent: Sep. 1, 2015

(54) ANTI-FOULING MATERIALS BASED ON POLY(β-PEPTOID)S

(75) Inventors: Li Jia, Hudson, OH (US); Lingyun Liu, Rochester Hills, MI (US)

(73) Assignee: The University of Akron, Akron, OH (US)

( * ) Notice: Subject to any disclaimer, the term of this patent is extended or adjusted under 35 U.S.C. 154(b) by 523 days.

(21) Appl. No.: 13/482,291

(22) Filed: May 29, 2012

(65) Prior Publication Data

US 2012/0298575 A1 Nov. 29, 2012

Related U.S. Application Data

(60) Provisional application No. 61/490,362, filed on May 26, 2011.

(51) Int. Cl.
*B32B 9/00* (2006.01)
*B32B 17/02* (2006.01)
(Continued)

(52) U.S. Cl.
CPC . *B01D 39/00* (2013.01); *A61F 2/02* (2013.01); *A61K 9/5005* (2013.01);
(Continued)

(58) Field of Classification Search
CPC .......... B01D 39/16; B01D 2239/0471; B01D 65/08; B01D 39/00; B01D 71/06; B01D 2239/0478; B32B 9/00; B32B 17/02; B32B 33/00; A61F 2/00; A61F 2/02; A61F 2205/0058; B08B 17/02; C02F 1/68; C25B 11/04; C25B 11/0442; C25B 11/0447; C25B 11/0473; C25B 11/0489; Y10T 428/31768; A61K 9/50; A61K 9/5005; A61K 9/5021; A61K 9/5052

USPC ........ 210/506, 698, 636; 422/1, 6; 428/478.2, 428/689, 543; 604/890.1, 891.1, 910; 204/290.01, 290.14; 424/422, 423
See application file for complete search history.

(56) References Cited

U.S. PATENT DOCUMENTS 4,111,933 A * 9/1978 Eckert et al. .................. 540/315
4,709,010 A * 11/1987 Holzemann et al. .......... 530/323
(Continued)

OTHER PUBLICATIONS

Publication: "The stability and immunogenicity of a protein antigen encapsulated in biodegradable microparticles based on blends of lactide polymers and polyethylene glycol", E. C. Lavelle et al, Department of Pharmaceutical Sciences, University of Nottingham University Park, Nottingham NG7 2RD , UK, published in Vaccine 17 (1999), pp. 512-529.*

(Continued)

*Primary Examiner* — Joseph Drodge
(74) *Attorney, Agent, or Firm* — Renner Kenner Greive Bobak Taylor & Weber

(57) ABSTRACT

Poly(β-peptoid)s selected from the group consisting of poly (N-methyl-β-alanine)s (PMeA) and poly(N-ethyl-β-alanine)s (PEtA) and polyl(methyl-β-alanine-co-ethyl-β-alanine) copolymers (P(MeA-co-EtA) are found to be good antifouling materials in that they resist protein adsorption. A process for protecting a surface of an object from protein adsorption comprises the steps of binding such poly(β-peptoid)s to the surface. A medical implant is coated with such poly(β-peptoid)s. A medical drug delivery device is coated with such poly(β-peptoid)s. A filtration device has pores coated with such poly(β-peptoid)s, and an object placed in freshwater or saltwater and having a surface in contact with the freshwater or saltwater has that surface coated with such poly(β-peptoid)s.

15 Claims, 10 Drawing Sheets

Scheme 1. Synthesis of poly(β-peptoid)s with a thiol terminus.

(51) Int. Cl.
*A61F 2/02* (2006.01)
*B32B 33/00* (2006.01)
*A61K 9/50* (2006.01)
*C25B 11/04* (2006.01)
*B01D 39/00* (2006.01)

(52) U.S. Cl.
CPC ............ *A61K 9/5021* (2013.01); *A61K 9/5052* (2013.01); *B32B 9/00* (2013.01); *B32B 17/02* (2013.01); *B32B 33/00* (2013.01); *C25B 11/0442* (2013.01); *C25B 11/0447* (2013.01); *C25B 11/0473* (2013.01); *B01D 2239/0471* (2013.01); *Y10T 428/31768* (2015.04)

(56) References Cited

U.S. PATENT DOCUMENTS

| | | | | |
|---|---|---|---|---|
| 5,496,914 | A * | 3/1996 | Wood et al. | 528/328 |
| 7,368,127 | B2 * | 5/2008 | Diana | 424/429 |
| 7,618,937 | B2 * | 11/2009 | Messersmith et al. | 514/1.1 |
| 2002/0151776 | A1 * | 10/2002 | Shawgo et al. | 600/345 |
| 2003/0161753 | A1 * | 8/2003 | MacPhee et al. | 422/1 |
| 2004/0258726 | A1 * | 12/2004 | Stupp et al. | 424/423 |
| 2006/0127438 | A1 * | 6/2006 | Hunter et al. | 424/422 |
| 2006/0241281 | A1 * | 10/2006 | Messersmith et al. | 530/324 |
| 2007/0026037 | A1 * | 2/2007 | Kloke et al. | 424/423 |
| 2007/0077275 | A1 * | 4/2007 | Haynie | 424/423 |
| 2007/0212393 | A1 * | 9/2007 | Patravale et al. | 424/423 |
| 2008/0051766 | A1 * | 2/2008 | Santini et al. | 604/890.1 |
| 2008/0286326 | A1 * | 11/2008 | Benco | 424/423 |
| 2009/0051766 | A1 * | 2/2009 | Shimbo et al. | 348/143 |
| 2010/0028719 | A1 * | 2/2010 | Messersmith et al. | 428/702 |
| 2012/0270800 | A1 * | 10/2012 | Verdine et al. | 514/19.4 |
| 2014/0072609 | A1 * | 3/2014 | Pacetti et al. | 424/423 |

OTHER PUBLICATIONS

Publication: "Proteins and cells on PEG immobilized silicon surfaces", Miqin Zhang et al, published in Biomaterials, vol. 19, (1998), pp. 953-960.*
Abstract of publication "Antifouling Poly(B-peptoid)s" Lin et al, Biomacromolecules, vol. 12(7), pp. 2573-2582, May 17, 2011.*
Publication: "Antifouling Poly(B-Peptoid)s", Lin et al, Biomacromolecules, vol. 12, pp. 2573-2582, May 17, 2011.*
Publication: "Polypeptoids from N-Substituted Glycine N-Carboxyanhydrides: Hydrophilic, Hydrophobic, and Amphiphilic Polymers with Poisson Distribution", Fetsch et al, Macromolecules, vol. 44, pp. 6746-6758, Aug. 4, 2011.*
Publication: "New Peptidomimetic Polymers for Antifouling Surfaces", Andrea Statz et al, Journal of American Chemical Society, vol. 127, pp. 7972-7973, 2005.*

* cited by examiner

US 9,120,040 B2

ANTI-FOULING MATERIALS BASED ON POLY(β-PEPTOID)S

CROSS-REFERENCE TO RELATED APPLICATIONS

This application claims priority to U.S. Provisional patent application No. 61/490,362, filed May 26, 2011, the entirety of which is incorporated herein by reference.

FIELD OF THE INVENTION

The present invention general relates to anti-fouling materials. More particularly, the present invention relates to poly (β-peptoid)s providing anti-fouling properties, and, in particular, relates to poly(N-methyl-β-alanine) (PMeA) and poly (N-ethyl-β-alanine) (PEtA) and copolymers of PMeA and PEtA, i.e., polyl(methyl-β-alanine-co-ethyl-β-alanine) or P(MeA-co-EtA).

BACKGROUND OF THE INVENTION

Nonspecific protein adsorption to implanted medical devices is believed to be the first step that leads to adverse events such as bacterial infection, blood clot formation, and fibrous encapsulation. Surfaces that resist protein adsorption, or "antifouling surfaces", are therefore critical for biomedical implants as well as other related biomedical applications such as drug delivery and engineering applications such as the prevention of marine and freshwater fouling. Poly(ethylene glycol) (PEG), oligo(ethylene glycol) (OEG) and their derivatives are the most commonly used nonfouling materials. However, they undergo oxidative degradation, especially in the presence of oxygen and transition metal ions, both of which are abundant in vivo. Recent studies show that surfaces covered with or without PEG polymers produced a similar degree of fouling in vivo. Several types of polymers have been developed as alternatives to PEG, including carbohydrate derivatives, poly(2-methyl-2-oxazoline), zwitterionic polymers, and polypeptoids. Among them, polypeptoids have been shown to provide long-term resistance to protein and cell adhesion. Though such non-fouling materials exist, there is a need in the art for other non-fouling (or anti-fouling) materials.

SUMMARY OF THE INVENTION

In one embodiment, this invention provides a process for protecting a surface of an object from protein adsorption, the process comprising the steps of binding a poly(β-peptoid) to the surface, the poly(β-peptoid) being selected from the group consisting of poly(N-methyl-β-alanine)s (PMeA) and poly(N-ethyl-β-alanine)s (PEtA) and polyl(methyl-β-alanine-co-ethyl-β-alanine) copolymers (P(MeA-co-EtA) and mixtures thereof.

In other embodiments, this invention provides a process as in paragraph [0003], wherein the poly(β-peptoid) is PMeA.

In other embodiments, this invention provides a process as in paragraphs [0003], wherein the poly(β-peptoid) is PEtA.

In other embodiments, this invention provides a process as in paragraph [0003], wherein the poly(β-peptoid) is P(MeA-co-EtA).

In other embodiments, this invention provides a process as in any of paragraphs [0003] through [0006], wherein the surface is a gold surface.

In other embodiments, this invention provides a process as in any of paragraphs [0003] through [0007], wherein the object is an electrode for a drug delivery microchip.

In other embodiments, this invention provides a process as in any of paragraphs [0003] through [0008], wherein in said step of binding, said poly(β-peptoid) includes a functional group X selected from a thiol group and dioxyphenylalanine.

In other embodiments, this invention provides a process as in any of paragraphs [0003] through [0009], wherein said functional group X is a thiol group such that the poly(β-peptoid) is a thiol-functionalized poly(β-peptoid), and, in said step of binding, the thiol-functionalized poly(β-peptoid) is bound to the gold surface by adsorption from solution, wherein a dilute solution of the thiol-functionalized poly(β-peptoid) is dissolved in an appropriate solvent and allowed to adsorb to the gold surface.

In other embodiments, this invention provides a process as in any of paragraphs [0003] through [0010], wherein the object is an electrode for a drug delivery microchip.

In other embodiments, this invention provides a process as in any of paragraphs [0003] through [0011], wherein the object is an object for placement in freshwater or saltwater.

In other embodiments, this invention provides a process as in any of paragraphs [0003] through [0012], further comprising the step of exposing the object to bodily fluids.

In other embodiments, this invention provides a process as in any of paragraphs [0003] through [0012], further comprising the step of exposing the object to freshwater or saltwater.

In other embodiments, the present invention provides a medical implant coated with a poly(β-peptoid) selected from the group consisting of poly(N-methyl-β-alanine)s (PMeA) and poly(N-ethyl-β-alanine)s (PEtA) and polyl(methyl-β-alanine-co-ethyl-β-alanine) copolymers (P(MeA-co-EtA).

In yet other embodiments, the present invention provides an object placed in freshwater or saltwater and having a surface in contact with the freshwater or saltwater, the surface being coated with a poly(β-peptoid) selected from the group consisting of poly(N-methyl-β-alanine)s (PMeA) and poly (N-ethyl-β-alanine)s (PEtA) and polyl(methyl-β-alanine-co-ethyl-β-alanine) copolymers (P(MeA-co-EtA).

In yet other embodiments, this invention provides a filtration device having pores coated with a poly(β-peptoid) selected from the group consisting of poly(N-methyl-β-alanine)s (PMeA) and poly(N-ethyl-β-alanine)s (PEtA) and polyl(N-methyl-β-alanine-co-N-ethyl-β-alanine) copolymers (P(MeA-co-EtA).

In other embodiments, this invention provides a medical drug delivery device with a surface having a poly(β-peptoid) selected from the group consisting of poly(N-methyl-β-alanine)s (PMeA) and poly(N-ethyl-β-alanine)s (PEtA) and polyl(N-methyl-β-alanine-co-N-ethyl-β-alanine) copolymers (P(MeA-co-EtA).

DETAILED DESCRIPTION OF ILLUSTRATIVE EMBODIMENTS

Poly(β-peptoid)s or poly(N-alkyl-β-alanine)s, as a class of polymer closely related to polypeptoids, can be conveniently synthesized in a living fashion by cobalt-catalyzed carbonylative polymerization of aziridines. Unlike polypeptoids, which have been broadly investigated for various biomedical applications, poly(β-peptoid)s have so far not been explored. During storage in an ambient environment, poly(N-methyl-β-alanine) (PMeA) and poly(N-ethyl-β-alanine) (PEtA) will be found to absorb a large amount of water. They therefore have all the common characteristics previously put forth for anti-fouling materials, namely, high water solubility, flexible backbone, charge neutrality, and hydrogen-accepting but not hydrogen-donating ability for hydrogen bonding. In this invention, PMeA and PEtA are created and described as useful as anti-fouling materials.

Figure 1:
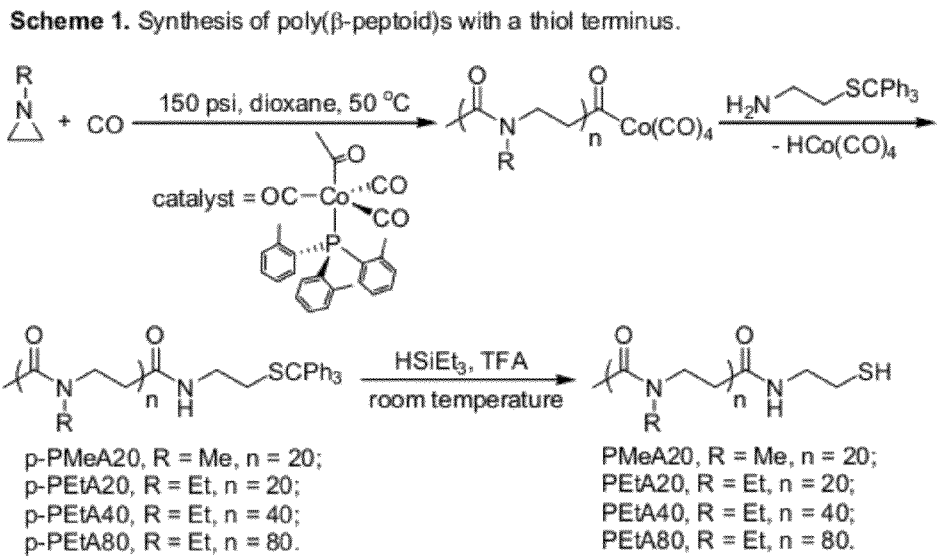
FIG. 1 provides a reaction scheme for the cobalt-catalyzed carbonylative polymerization of N-methylaziridine or N-ethylaziridine, the resulting polymer thereafter being functionalized by a thiol group.

In accordance with this invention, PMeA and PEtA are formulated according to the general scheme shown in FIG. 1. Monomer selected from N-methylaziridine or N-ethylaziridine is polymerized through cobalt-catalyzed carbonylative polymerization in the presence of dioxane. It will be appreciated that, though not shown in FIG. 1, it is also acceptable to provide the monomer as a mixture of N-methylaziridine and N-ethylaziridine and thereby create polyl(N-methyl-β-alanine-co-N-ethyl-β-alanine) copolymers (or P(MeA-co-EtA)). In particular embodiments, a reaction vessel is fed a catalyst solution of cobalt catalyst (namely, $CH_3COCo(CO)_3PAr_3$ (Ar=o-tolyl)) and 1,4 dioxane under a carbon monoxide atmosphere. The reactor is pressurized to a pressure of from 15 to 1500 psi and heated to a temperature of from 25 to 120° C., and the monomer is added to the reaction vessel in a solution of 1,4 dioxane and further pressurized to a pressure of from 15 to 1500 psi and stirred. The polymerization may be monitored by ATR-IR. The polymerization results in the forming of a poly(β-peptoid) with a Co(CO)4 terminus resulting from the catalyst. Using co-monomers N-methylaziridine and N-ethylaziridine results in the forming of a poly(β-peptoid-co-β-peptoid) with a Co(CO)4 terminus.

It has been found that these poly(β-peptoid)s or poly(β-peptoid-co-β-peptoid)s resist protein adsorption, and, thus, in accordance with embodiments of this invention these polymers and copolymers are used to coat surfaces to serve as protective anti-fouling coatings. To use them in this manner, the Co(CO)4 terminus is replaced by any suitable entity to allow for the chemical or physical attachment of the poly(β-peptoid) or poly(β-peptoid-co-β-peptoid) to a surface. This is generally represented in the formulae below: for PMeA:

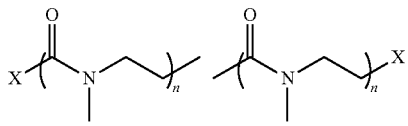

for PEtA:

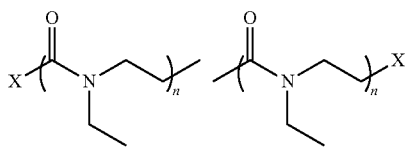

and for P(MeA-co-EtA)

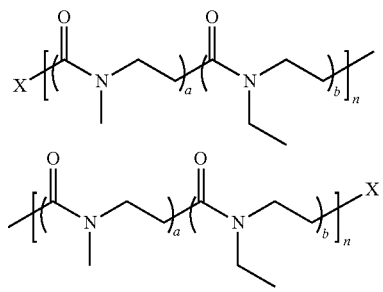

wherein X is any end group at either the C or N terminus of the polymer chain, the end group X being suitably chosen to allow for the chemical or physical attachment of the anti-fouling polymer/copolymer to a desired surface. The variables n, a and b are provided to show that the polymers and copolymers may be provided with differing degrees of polymerization.

Surfaces to which the anti-fouling materials of this invention may be bound or coated include, by way of example only, metals (e.g., gold, titanium), amine-functionalized surfaces, hydroxyl-functionalize surfaces, glass, silocone wafers, and any silicon dioxide surface. For gold surfaces, the X group may be chosen to be thiol (SH) or dioxyphenylalanine (DOPA). DOPA may also be employed to provide functionality to bind to other metals, such as titanium, platinum, stainless steel and metal oxides such as $TiO_2$ and $Al_2O_3$, and also works well for binding to amine-functionalized surfaces, hydroxyl-functionalize surfaces and hydrophobic surfaces. For binding to glass, silicone wafers or any materials with $SiO_2$ coating, the X group may be chosen to be a silane $((CH_3O)_3Si)$. Again, this is understood to be exemplary only, and other groups may be employed for binding to these or other types of surfaces.

In some embodiments, the surface to be coated is a surface of an object or device placed in freshwater or saltwater. These may include support structures extending into freshwater or saltwater (e.g., dock and pier supporting columns and other support structures) and objects such as bouys or watercraft and components thereof (e.g. rudders or propellers)

The development of antifouling coatings on gold is very important. Gold has been applied for applications such as electrodes for a drug delivery microchip and for neural implants. For example, in drug delivery microchips, the active drug is stored in a microreservoir covered with a gold membrane electrode and released by electrochemical dissolution of the thin gold membrane. Significant biofouling in vivo, however, may affect the drug-eluting capability of such michrochips, and thus, anti-fouling coatings such as those taught here will find specific application in coating the gold membrane electrode. For neural device applications, biofouling on electrodes causes increased impedance, which makes it difficult to record electrical signals, and the anti-fouling coatings of this invention will be useful coatings for neural devices.

In the embodiment exemplified in FIG. 1, the X group is made a thiol for the purpose of binding the poly(β-peptoid) or poly(β-peptoid-co-β-peptoid) to gold. The residual cobalt is removed by treating the crude product with $Na_2S$ and filtering through activated carbon. The resulting polymer is then end functionalized by injecting S-trityl cysteamine (in dioxane) into the reactor and allowing to react to completion, typically from 0.1 to 4 hours. The resultant polymer is now terminated with a trityl group. As seen in FIG. 1, the reaction yields PMeA or PEtA, depending upon the starting aziridine. A starting mixture of N-methylaziridine and N-ethylaziridine yields P(MeA-co-EtA). In the case of PMeA, the number average degree of polymerization, $X_n$, is limited to 20 or below due to the crystallization of PMeA during polymerization, while, in the case of PEtA, $X_n$ is dependent upon the catalyst-to-aziridine ratio.

The trityl group of the resultant trityl protected polymer is then replaced with a thiol terminus by reaction with triethylsilane. The trityl protected polymer is dissolved in anhydrous $CH_2Cl_2$ and trifluoroacetic acid and is cooled to 0° C., at which time the triethylsilane is added and the solution permitted to warm up to room temperature to be concentrated to dryness. The residue is dissolved in chloroform and the polymer, now thiol terminated, is precipitated by a slow addition of either.

It is well appreciated that the sulfur of the thiol group has a strong affinity for noble metals, and thus, the thiol-functionalized poly(β-peptoid)s of this invention can be readily bound to such surfaces. The poly(β-peptoid) can be coated onto the surface of noble metals, and particularly gold, by adsorption from solution, wherein a dilute solution of the thiol-functionalized poly(β-peptoid) is dissolved in an appropriate solvent, such as ethanol, and allowed to adsorb to the surface. A specific example is provided herein in the Examples section.

The discovery that the particular poly(β-peptoid)s disclosed herein resist protein adsorption and thus will serve well as anti-fouling coatings for a variety of items as already noted above. An exemplary synthesis of PMeA and PEtA is provided below in the Examples section, and these poly(β-peptoid)s are bound to a gold surface to characterize their protein adsorption and prove their novel use as anti-fouling materials. Their production can also be found in Jia, L., et al., J. Am. Chem. Soc. 2002, 124, 7282-7283.11 should be broadly appreciated that the present discovery of anti-fouling properties in PMeA and PEtA lead to a novel process for protecting a surface of an object from protein adsorption. The process can be broadly characterized as comprising the steps of binding a poly(β-peptoid) to the surface, the poly(β-peptoid) being selected from the group consisting of poly(N-methyl-β-alanine)s (PMeA) and poly(N-ethyl-β-alanine)s (PEtA) and polyl(methyl-β-alanine-co-ethyl-β-alanine) copolymers (P(MeA-co-EtA). The selection of surfaces to be protected is unlimited, and those of ordinary skill in the art will be readily able to secure the poly(β-peptoid)s to a desired surface through appropriate functionalization as taught herein, for example with the binding to a gold surface. Thus, in other embodiments, this invention provides a medical implant coated with a poly(β-peptoid) selected from the group consisting of poly(N-methyl-β-alanine)s (PMeA) and poly(N-ethyl-β-alanine)s (PEtA) and poly(N-methyl-β-alanine-co-N-ethyl-β-alanine) copolymers (P(MeA-co-EtA). And in yet other embodiments, the present invention provides an object placed in freshwater or saltwater and having a surface in contact with the freshwater or saltwater, the surface being coated with a poly(β-peptoid) selected from the group consisting of poly(N-methyl-β-alanine)s (PMeA) and poly(N-ethyl-β-alanine)s (PEtA) and polyl(methyl-β-alanine-co-ethyl-β-alanine) copolymers (P(MeA-co-EtA). In other embodiments, this invention provides a filtration device having pores coated with a poly(β-peptoid) selected from the group consisting of poly(N-methyl-β-alanine)s (PMeA) and poly(N-ethyl-β-alanine)s (PEtA) and polyl(N-methyl-β-alanine-co-N-ethyl-β-alanine) copolymers (P(MeA-co-EtA). In other embodiments, this invention provides a medical drug delivery device with a surface having a poly(β-peptoid) selected from the group consisting of poly(N-methyl-β-alanine)s (PMeA) and poly(N-ethyl-β-alanine)s (PEtA) and polyl(N-methyl-β-alanine-co-N-ethyl-β-alanine) copolymers (P(MeA-co-EtA).

In light of the foregoing, it should be appreciated that the present invention significantly advances the art by providing poly(β-peptoid)-based anti-fouling materials for coating surfaces for a wide variety of applications. Particularly, the present invention advances the art by the discovery that poly (N-methyl-β-alanine) (PMeA), poly(N-ethyl-β-alanine) (PEtA) and polyl(methyl-β-alanine-co-ethyl-β-alanine) copolymers can be employed as anti-fouling materials, particularly as materials that resist protein adsorption. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Materials

N-Ethylaziridine and N-methylaziridine were synthesized using a modified method from the literature, Reeves, W. A.; Drake, G. L. J.; Hoffpauir, C. L., J. Am. Chem. Soc. 1951, 73, 3522-3523. The monomers were stirred over Na/K alloy at room temperature for at least two weeks and kept over Na/K alloy. They must be freshly vacuum-transferred before use. The purity of the monomer is crucial for quantitative conversion of the monomer to the polymer and for quantitative end-group functionalization. Synthesis of the catalyst $CH_3COCo(CO)_3PAr_3$ (Ar=o-tolyl) was previously reported by Darensbourg, D. J.; Phelps, A. L.; Le Gall, N.; Jia, L. J. Am. Chem. Soc. 2004, 126, 13808-13815. Anhydrous 1,4-dioxane was purchased from Sigma-Aldrich and used without further purification as the polymerization solvent.

Human plasma fibrinogen (Fg), bovine serum albumin (BSA), chicken egg white lysozyme (Lyz), and phosphate buffered saline (PBS) (pH 7.4, 10 mM, 138 mM NaCl, 2.7 mM KCl) were purchased from Sigma-Aldrich (Milwaukee, Wis.). Pooled human serum and plasma were purchased from Biochemed services (Winchester, Va.). Ethanol (absolute 200 proof) was purchased from PHARMCO-AAPER. Water used in protein adsorption experiments was purified using a Millipore water purification system with a minimum resistivity of 18.0 MΩ·cm.

Characterization of Polymers

Nuclear magnetic resonance (NMR) experiments were performed on either Varian Mercury 300-MHz or Varian NMRS 500-MHz instruments. Solvent peaks were used as the reference for chemical shifts. Gel permeation chromatography (GPC) was performed using a Tosoh EcoSEC system equipped with a refractive index detector. Trifluoroethanol was used as the eluent to avoid anomalous chromatograms observed when common organic solvents such as chloroform were used as the eluent. The flow rate was 0.35 mL/min, and the column temperature was 35° C. Monodisperse poly(methyl methacrylate) standards were used to calibrate the column. Matrix-Assisted Laser Desorption/Ionization Time-Of-Flight Mass Spectrometry (MALDI-TOF MS) measurements were performed on a Bruker UltraFlex III mass spectrometer. Dithranol was used as the matrix compound. Sodium trifluoroacetate was used as the cationization agent. The sample, matrix and cationization agent were mixed in a 2:10:1 ratio and dissolved in 1:1 tetrahydrofuran/chloroform (10 mg/mL). Approximately 0.5 μL of this mixture was deposited onto the sample holder and allowed to dry before insertion into the vacuum system. All quoted mass-to-charge (m/z) ratios are monoisotopic, containing the most abundant isotopes of the elements present.

Synthesis of Thiol-Terminated PMeA and PEtA

The polymerizations were run in a 300-mL stainless steel reactor (Autoclave Engineer) equipped with a mechanical stir and thermal couple. A stainless-steel tube was fitted to the top of the reactor via a ball-valve joint as reservoir for addition of the monomer and chain-terminating reagent. The reactor is located in a well-ventilated hood, around which CO detectors are placed. The reaction system is pumped overnight before use. Under a gentle CO flow, the catalyst solution (320 mg, 0.65 mmol in 10 mL anhydrous 1,4-dioxane) prepared under a CO atmosphere and anhydrous 1,4-dioxane (180 mL) was added into the autoclave. The reactor was pressurized to 100 psi and heated to 50° C. with an external heating jacket. Then, a dioxane solution of monomer was added through the addition tube pressurized to 150 psi while the reactor was mechanically stirred at 500 rpm. The polymerization was monitored by ATR-IR via a SICOM probe (ReactIR 4000, Mettler-Toledo) attached to the bottom of the reactor. When the polymerization reached completion (catalyst turnover frequency=20 h$^{-1}$), S-trityl cysteamine (840 mg, 2.61 mmol in 20 mL dioxane) was injected into the reactor via the slightly over-pressurized addition tube. The reaction was stirred for another 3 h, and the pressure was released.

The dioxane solution and the solid polymer was poured into an aqueous solution of excess Na$_2$S and stirred for 2 h. The resulting black CoS cannot be removed by simple filtration. All solvents were removed on a rotary evaporator, and the residue was extracted by chloroform (3×10 mL). The combined black chloroform solution was passed through a 4-cm long activated carbon column and became clear. The solution was then concentrated to about 5 mL, and the white product was precipitated by addition of ether. The yields of the PEtA polymers were ~65%, and the yield of the PMeA20 polymer was 51%.

Cleavage of the Trityl Protective Group

Under a nitrogen atmosphere, the above trityl-protected polymer (0.116 mmol) was dissolved in anhydrous CH$_2$Cl$_2$ (2 mL) and trifluoroacetic acid (5 mL). The solution was cooled to 0° C., at which temperature triethylsilane (0.2 mL) was added into the above solution. The solution was then allowed to warm up to room temperature, stirred for 4 h, and concentrated to dryness. The residue was dissolved in 3 mL of chloroform, and the thiol-functionalized polymer was precipitated by slow addition of ether. The isolated yields were ~90%.

Grafting the End-Functionalized Polymers onto the Gold-Coated SPR Sensing Chips

Thiol-functionalized polymer solutions (1 mM) were prepared using a mixture of ethanol and water as the solvent. Ethanol was a poor solvent for PMeA and PEtA, and water was added to completely dissolve the polymer. The solvent mixtures used to graft PEtA20, PEtA40, PEtA80, and PMeA20 were 80%, 85%, 85%, 85%, and 80% (v/v) ethanol, respectively. Prior to grafting, the gold-coated chips were cleaned by irradiation under UV/ozone for 20 min, rinsed extensively with deionized water and ethanol, and dried with N$_2$. The cleaned chips were then soaked in the polymer solution overnight at room temperature. Finally, the polymer-grafted chips were rinsed extensively with ethanol and water before being dried with a gentle N$_2$ stream.

Characterization of the Polymer Surface

The static contact angle of water on each polymer-grafted surface was measured using a Rame-Hart contact angle goniometer (model 100-00, Mountain Lakes, N.J.) under ambient laboratory conditions. The droplet size of deionized water was 10 μL. The measurements were made every minute for 10 min and repeated three times for each sample.

The X-ray photoelectron spectroscopy (XPS) measurements were made at Case Western Reserve University SCSAM surface analysis facility, using a PHI VersaProbe XPS microprobe (Physical Electronics, Chanhassen, Minn.) with a monochromatic Al Kα source. The spectra were acquired at a pass energy of 93.9 eV. Initial survey scans (0-1000 eV binding energy, 45°) were followed by detailed scans for carbon, oxygen, nitrogen, sulfur, and gold. Angle-resolved XPS spectra were collected at take-off angles of 10, 45, and 80° relative to the surface. All spectra were referenced by setting the C 1s peak to 285 eV. PHI MultiPack data analysis software was used to calculate the elemental compositions from the peak areas.

Protein Adsorption by SPR

A custom-built four channel SPR spectrometer was used to evaluate the resistance of the polymer-grafted surfaces to protein adsorption. The SPR spectrometer measures the change in the resonant wavelength at a fixed angle. The SPR sensing chip was prepared by coating an adhesion-promoting titanium layer (~2 nm) and a surface plasmon-active gold layer (~50 nm) by electron beam evaporation onto the glass substrate. The SPR chip was then attached to the base of the prism and optical contact was established using a refractive index matching fluid (Cargille). A four-channel Teflon flow cell with four independent small chambers was used to hold the liquid samples during the experiments. A peristaltic pump (Ismatec) was used to deliver the liquid samples to the four chambers of the flow cell. The flow rate of 0.05 mL/min was used throughout the experiments. One of the four channels was used as a reference channel to compensate signal changes caused by fluctuation such as flow disturbance and temperature shift while the other three were used as sensing channels. The net compensated response was obtained by subtracting the signal of the reference channel from that of the sensing channel.

A typical SPR experiment was carried out as follows. After the SPR chip was coated with the polymer as described above, the chip was mounted onto the prism and the SPR sensor was stabilized with PBS buffer for 5 min. Then, a 1 mg/mL protein solution of Fg, BSA, or Lyz in PBS, 10% blood serum in PBS, 100% blood serum, 10% blood plasma in PBS, or 100% blood plasma were flowed over the polymer-grafted sensing chip for 10 min, followed by flushing the surface with PBS for 5 min to remove the reversibly bound protein. Adsorption of protein on the bare gold surface without polymer modification was used as control for comparison.

The amount of the adsorbed protein is proportional to the wavelength shift from the baseline before protein adsorption to the one after buffer washing. The correlation of the SPR wavelength shift and the amount of adsorbed protein was calibrated based on the quantitative method established by Homola and coworkers. Surface coverage of the adsorbed protein, in mass per area, can be expressed as $$\Gamma = \frac{\Delta\lambda}{S_S} \cdot \frac{h}{(dn/dc)_{vol}} \quad (1)$$

where $\Gamma$ represent surface coverage of the analyte, $\Delta\lambda$ is the wavelength shift, $S_S$ denotes the spectral sensitivity of the SPR sensor to a surface refractive index change, h is the thickness of the adsorbed analyte layer, and $(dn/dc)_{vol}$ is the volume refractive index increment of the analyte.

As the layer thickness, h, is much smaller than the penetration depth of the field of the surface plasmon, $L_{pd}$, surface refractive index sensitivity ($S_S$) is proportional to the bulk refractive index sensitivity ($S_B$) and the ratio of the layer thickness and the penetration depth of the surface plasmon:

$$S_S = 2S_B \frac{h}{L_{pd}}.$$

Therefore, the protein surface coverage can be written as $$\Gamma = \frac{\Delta\lambda}{2S_B} \cdot \frac{L_{pd}}{(dn/dc)_{vol}} \quad (2)$$

For our SPR sensor operating at the wavelength of 750 nm ($L_{pd}\approx310$ nm, $S_B\approx5500$ nm/RIU) and a typical refractive index increment for proteins $(dn/dc)_{vol}=0.18$ ml/g, the above equation suggests that a 1-nm wavelength shift corresponds to a protein surface coverage of ~150 pg/mm².

Results and Discussion

Synthesis and Characterization of PMeA and PEtA

Thiol-terminated PMeA and PEtA for grafting to the SPR-sensing chips were synthesized according to the reaction scheme of FIG. 1. The carbonylative polymerizations of N-methylaziridine and N-ethylaziridines were carried out under the typical conditions that were previously established using the cobalt catalyst. The polymerization was terminated by S-trityl cysteamine in situ after the complete consumption of the aziridine monomer to give p-PEtA20~p-PEtA80 (the number following the acronym indicates the number-average degree of polymerization, $X_n$, anticipated from the catalyst-to-aziridine ratio) and p-PMeA20. The range of $X_n$ achievable for PMeA is limited to 20 or below due to crystallization of PMeA during polymerization. The residual cobalt was removed by treating the crude product with Na₂S followed by filtration through a short activated carbon column. Cobalt contamination in the so-treated products was below the detection limit of inductively coupled plasma-optical emission spectrometry (<3 ppm). The yields were ~65% for p-PEtA20~p-PEtA80 and ~50% for p-PMeA20 after removal of cobalt.

Figure 2A:
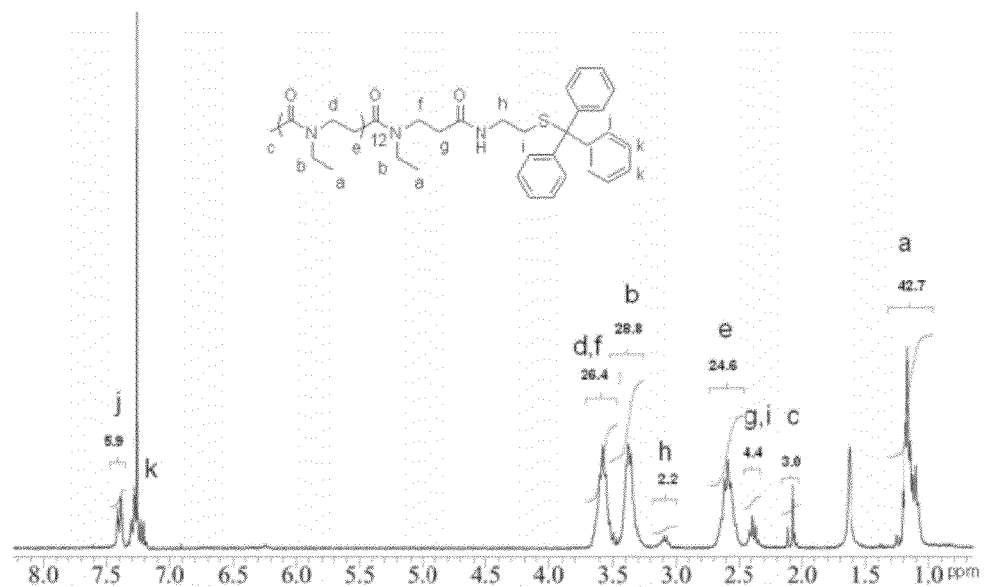
FIG. 2(a) shows the $^1$H NMR spectrum of p-PEtA10 in CDCl$_3$ with peak assignments and peak-area integrations, and FIG. 2(b) $^1$H,$^1$H-COSY spectrum of p-PEtA10, the PEtA10 being terminated with a trityl group.
Figure 2B:
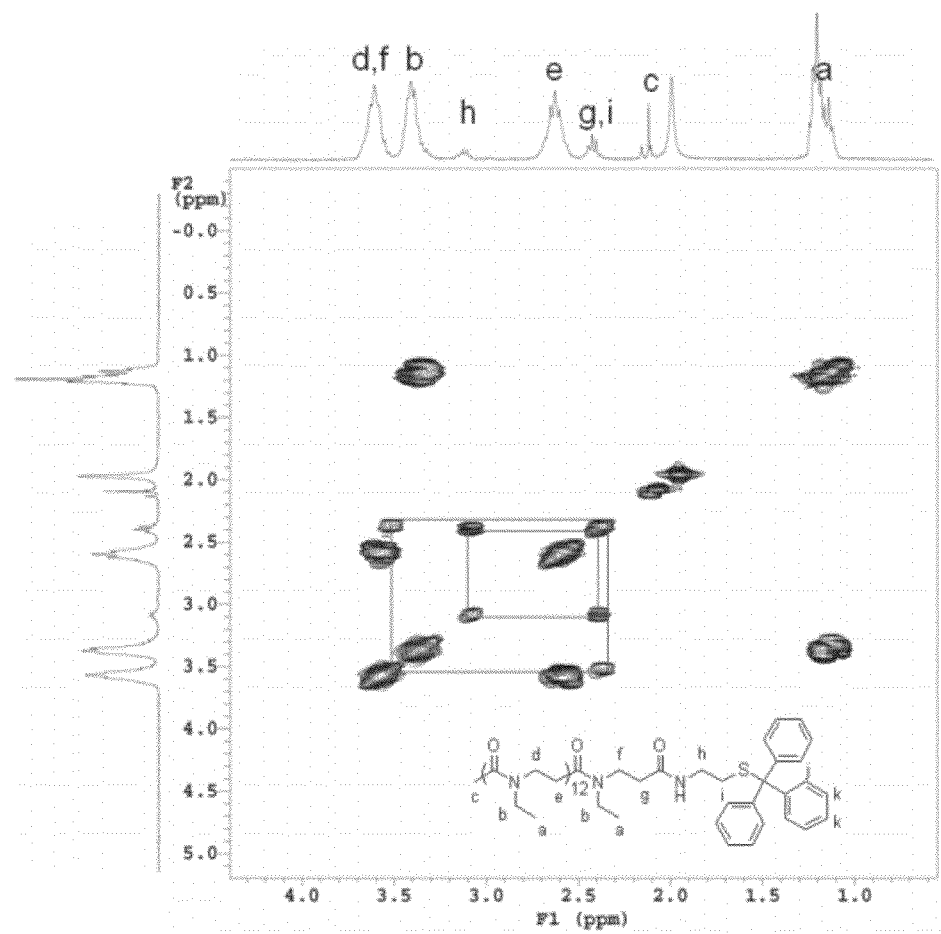

Detailed structural characterizations of the end-functionalized polymers are most conveniently performed at this stage when the trityl protective group is still attached to the thiol chain end. Proton nuclear magnetic resonance (¹H NMR) spectroscopy clearly confirms the presence of the anticipated end group (FIG. 2). The peak-area integrations of the acetyl protons and the trityl aromatic ortho protons in all samples are approximately in the expected 1:2 ratio within experimental error, indicating that the chain-end functionalization was relatively complete. Assignments of the ¹H peaks of the cysteamine-derived end group in the aliphatic region were made on the basis of the chemical shifts and proton-proton correlation spectroscopy (¹H,¹H-COSY) (FIG. 3) using a p-PEtA10 sample to make the correlations readily observable. The $X_n$ values were determined by end group analysis using the ¹H peaks of the acetyl end group and the repeat units. The experimentally determined $X_n$ values were consistent with the anticipated values, namely, the aziridine-to-catalyst ratios. The relative molecular weights determined by GPC using monodisperse poly(methyl methacrylate) standards were more than one order of magnitude higher than the expected values. We deem these values erroneous likely because the polyamides are much better solvated by trifluoroethanol, which is one of the mobile phases suitable for poly(9-peptoid)s, than the poly(methyl methacrylate) standards are. The polydispersity indices (PDIs) characterized by GPC range from 1.1-1.5. The experimentally determined $X_n$ and PDI values are summarized in Table 1.

TABLE 1

Number-average degrees of polymerization and polydispersity indices of end-functionalized poly(☐-peptoid)s, wherein the $X_n$ values are obtained with end group analysis and the PDI values are obtained with GPC.

|  | p-PEtA20 | p-PEtA40 | p-PEtA80 | p-PMeA20 |
|---|---|---|---|---|
| $X_n$ | 22.4 | 40.4 | 78.3 | 23.1 |
| PDI | 1.42 | 1.14 | 1.11 | 1.48 |

Figure 3:
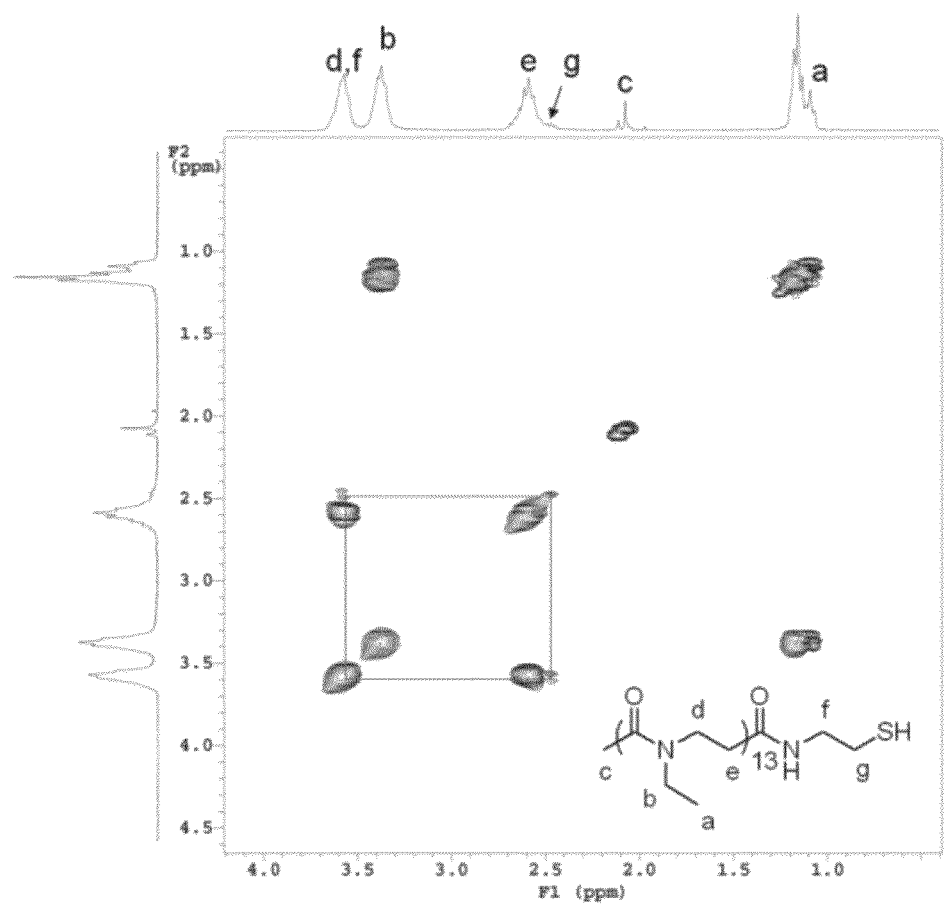
FIG. 3 shows the $^1$H,$^1$H-COSY of PEtA10 and peak assignments, the PEtA10 being terminated with a thiol group.
Figure 4A:
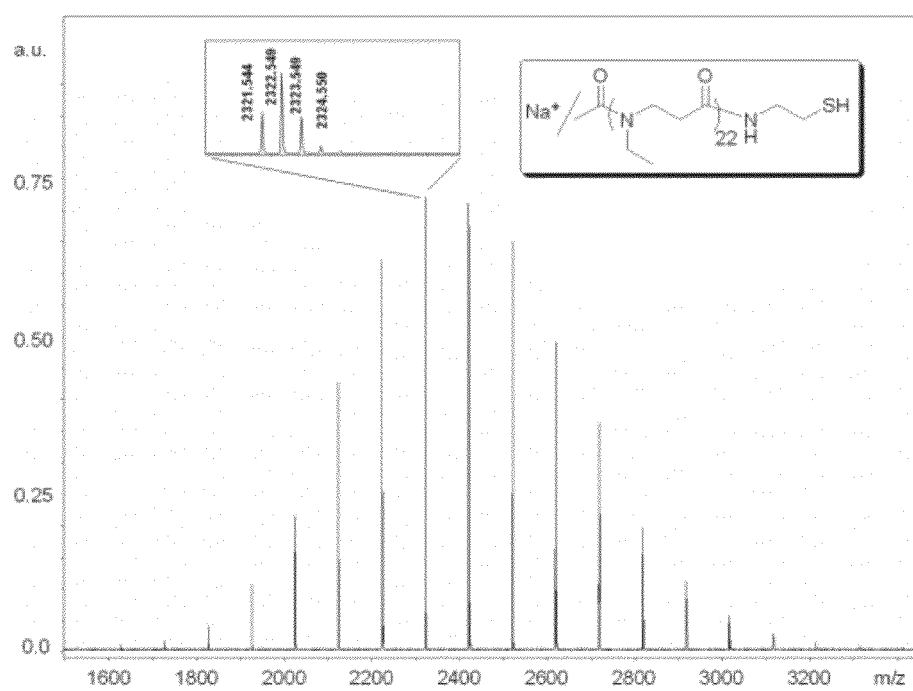
FIG. 4(a) provides MALDI-TOF mass spectra of PEtA20 and FIG. 4(b) provides MALDI-TOF mass spectra of PMeA20, the insets revealing the isotope distribution and the structure of the specific ion.
Figure 4B:
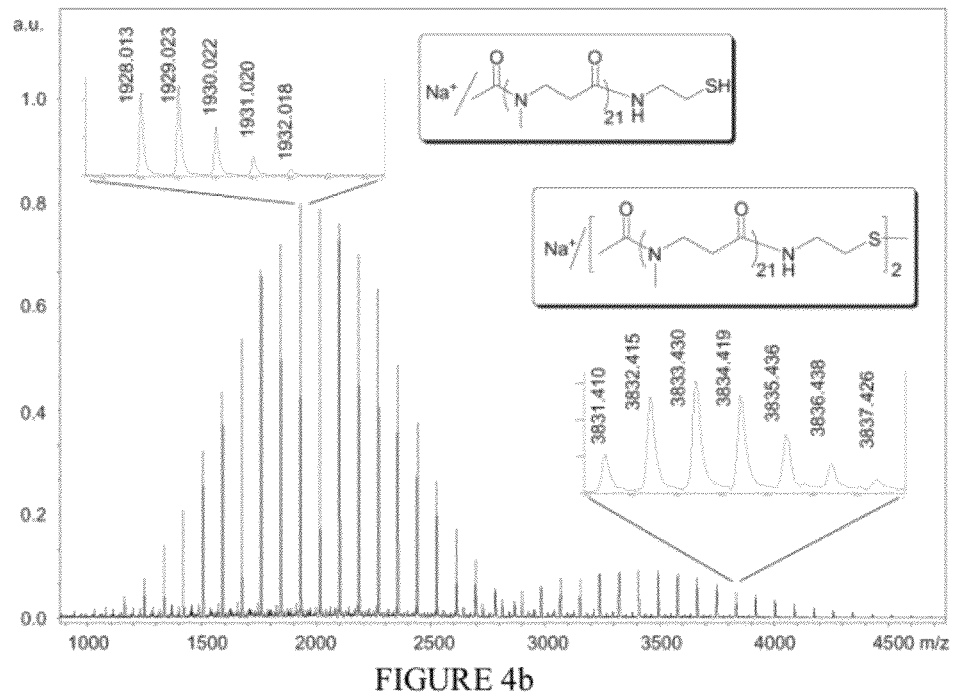

Cleavage of the trityl protective group was essentially quantitative (FIG. 1), affording the thiol-terminated PMeA and PEtA in ~90% isolated yields. ¹H NMR spectroscopy provided little information about the cysteamine-derived end group because the corresponding peaks overlapped with those of the repeat units after deprotection (FIG. 3). The best evidence for the presence of the cysteamine-derived end group came from MALDI-TOF MS (FIG. 4). PMeA20 and PEtA20 were used as the representative samples because their low-molecular weights render them amenable for efficient laser desorption. Only one cluster of ions was observed in the mass spectrum of PEtA20. The mass/charge ratios (m/z), m/z=22.99+119.07+99.07n, indicate that these ions are the sodium complexes of the anticipated cysteamine-terminated chains. The most abundant peak corresponds to n=22, consistent with $X_n$ determined by end group analysis. In the mass spectrum of PMeA20, two clusters of ions were observed with m/z=23+119.07+85.06n and m/z=23+2(118.06+85.06n). The major cluster can be assigned to the sodium complexes of the cysteamine-terminated chains. The most abundant peak corresponds to n=21, consistent with $X_n$ determined by end group analysis. The minor cluster corresponds to the sodium complexes of the dimerized chains linked by disulfide bonds due to oxidative coupling of the thiol end group. The presence of the dimeric chains is acceptable since disulfides and thiols form self-assembled monolayers (SAMs) on gold with the same structural and bonding characters.

Characterization of Polymer-Grafted Gold Surface

Figure 5:
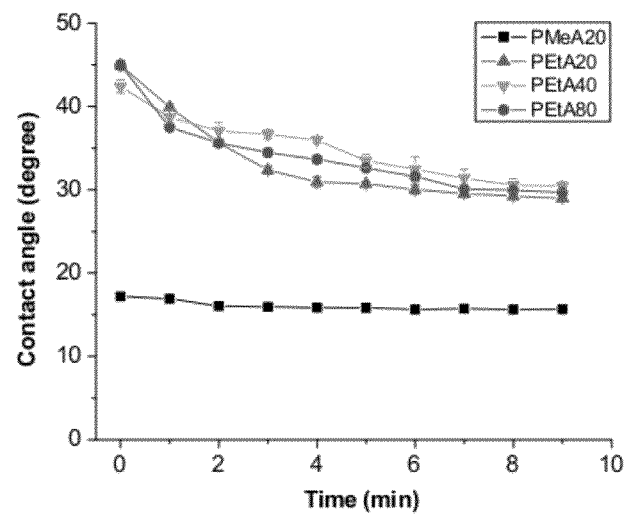
FIG. 5 provides water-contact angles of various poly(β-peptoid)-grafted surfaces.
Figure 6A:
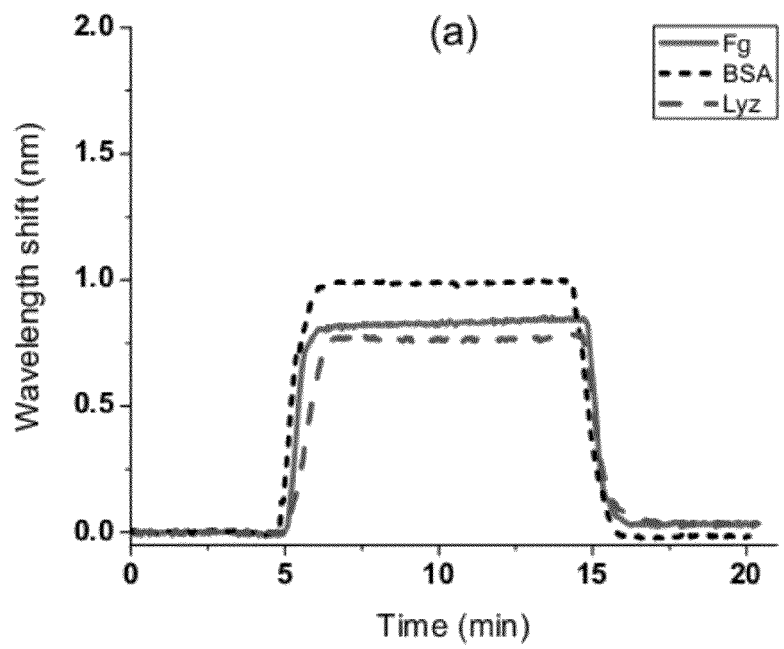
FIG. 6 provides SPR sensorgrams of Fg, BSA, and Lyz solutions flowing over the surfaces of PEtA20 FIG. 6(a), PEtA40 FIG. 6(b), PEtA80 FIG. 6(c), PMeA20 FIG. 6(d), and bare gold FIG. 6(e)
Figure 6B:
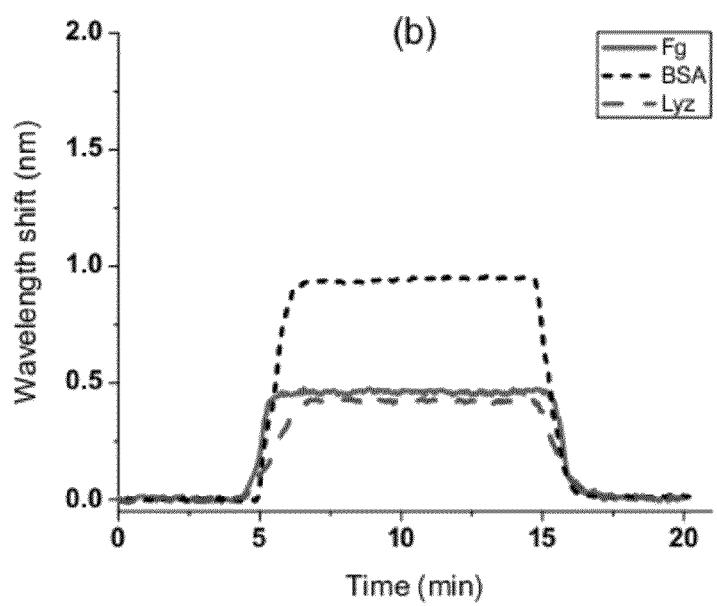
Figure 6C:
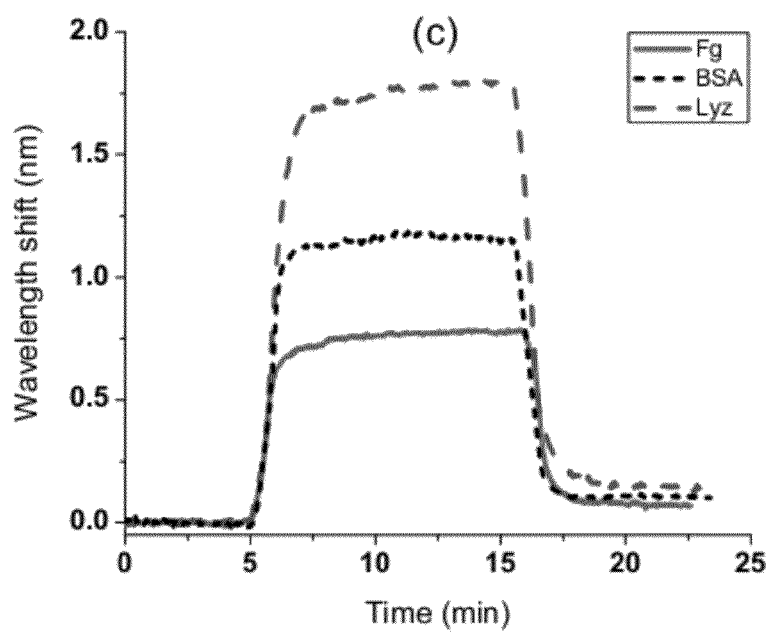
Figure 6D:
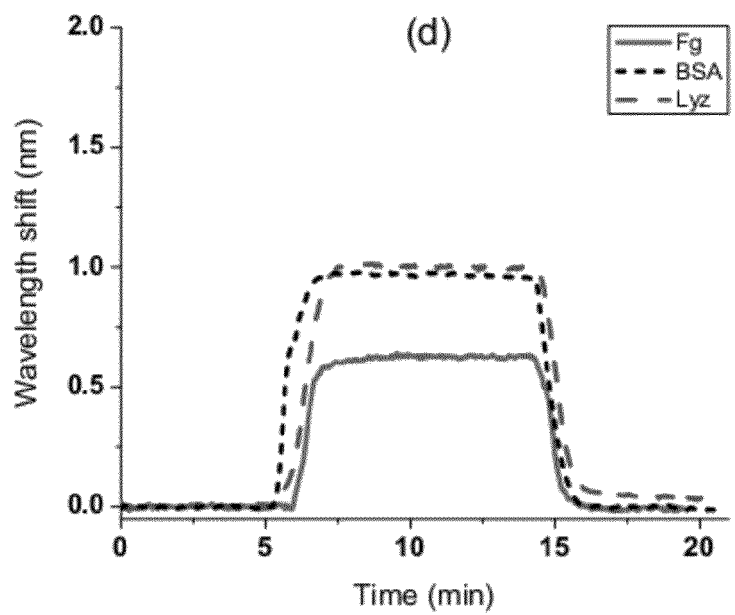
Figure 6E:
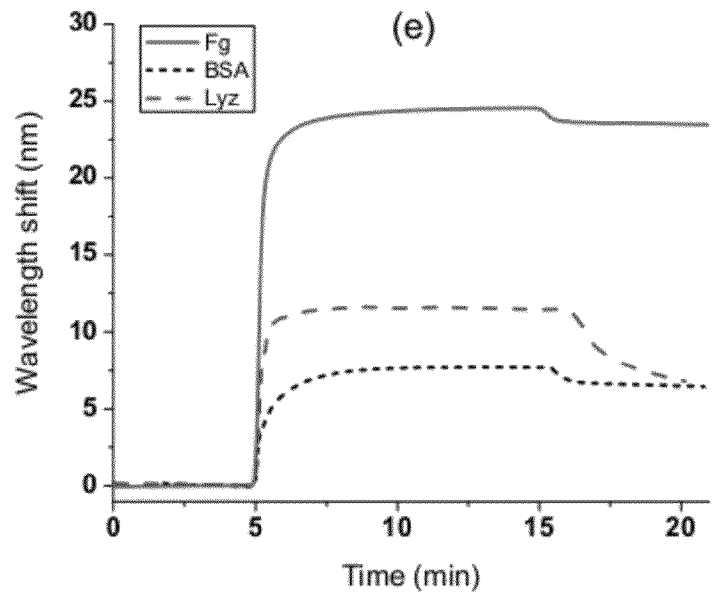

Near-cloud-point solutions of PMeA and PEtA in a mixture of ethanol and water were used for grafting the gold surface of the SPR-sensing chip. The compact chain conformation in the near-cloud-point solution should give a high grafting density. The chips were soaked in the polymer solutions overnight to ensure maximal grafting density. The static water-contact angles on the resulting PMeA- and PEtA-grafted surfaces were measured as a function of time as shown in FIG. 5. The PEtA-grafted surfaces exhibit increasing water wettability with time but reach the same steady-state contact angle within experimental error. The change in water wettability with time is not obvious on the PMeA-grafted surface. All PEtA- and PMeA-grafted surfaces are hydrophilic. The contact angle of the PMeA-grafted surface is markedly lower than those of PEtAs, consistent with the expectation that PMeA is more hydrophilic than PEtA because of the difference in their hydrocarbon content.

The elemental compositions and their depth profiles of the grafted polymers on gold were examined using angle-resolved X-ray photoelectron Spectroscopy (XPS) as summarized in Table 2. The carbon, oxygen, and nitrogen ratios had relatively low variations as a function of takeoff angle. Most of them are in good agreement with the anticipated values within ±20% error. The only exception is the PEtA20-grafted sample, the carbon content of which is lower than the anticipated value by as much as 38%. Since the PEtA20-grafted surface demonstrated an excellent nonfouling property as will be shown below, we consider this data point an outlier due to fortuitous experimental errors. Sulfur and gold were detected even at the 10° takeoff angle in all samples, indicating that the polymer layers are thinner than the attenuation length (~5 nm).

TABLE 2

Elemental composition of poly(□-peptoid)-grafted surfaces determined by XPS at three takeoff angles, wherein the anticipated C:O:N ratios of PEtA- and PMeA-grafted surfaces are 5:1:1 and 4:1:1, respectively.

| Takeoff angle (°) | C:O:N ratio | | | |
|---|---|---|---|---|
| | PEtA20 | PEtA40 | PEtA80 | PMeA20 |
| 10 | 3.1:1.1:1.0 | 4.9:0.9:1.0 | 4.8:1.0:1.0 | 4.5:1.0:1.0 |
| 45 | 3.7:1.0:1.0 | 5.2:1.1:1.0 | 4.0:0.9:1.0 | 3.8:0.9:1.0 |
| 80 | 4.0:1.4:1.0 | 5.1:1.1:1.0 | 5.4:1.1:1.0 | 4.0:1.0:1.0 |

Single Protein Adsorption

SPR spectroscopy is highly sensitive for detection of surface adsorbates. The theoretical detection limit of surface coverage is proposed to be 0.91 pg/mm$^2$ by Homola. The practical detection limit is typically a few to ten pg/mm$^2$ as previously estimated by Ladd et al and Ma et al, respectively. The SPR instrument used in this study has a similar detection limit. In a typical adsorption experiment, the SPR chip modified with PMeA or PEtA was first exposed to phosphate buffered saline (PBS) to establish a stable baseline. A protein solution at the 1 mg/mL concentration was then passed over the surface for 10 min. After exposure to the protein solution, the chip was again exposed to the PBS buffer. The SPR wavelength was recorded at a fixed incidence angle during the entire process. The difference between the final wavelength and the initial baseline is used to calculate the amount of adsorbed protein (see Experimental Methods for details). Human plasma fibrinogen (Fg), bovine serum albumin (BSA), chicken egg white lysozyme (Lyz) were used as representative proteins in this work, encompassing a range of molecular weight (MW=340 kDa, 67 kDa, and 14.7 kDa, respectively), structural stability with respect to denature, and isoelectronic point (pI=5.5, 4.7, and 11.1, respectively). Among them, Fg is commonly used to evaluate the nonfouling property of materials due to its ability to easily adsorb to a wide range of substances and its roles in the inflammatory response in vivo and blood clot formation when a medical device is exposed to blood. FIG. 6 gives representative SPR sensorgrams of Fg, BSA, and Lyz adsorption onto PMeA20, PEtA20, PEtA40, and PEtA80 surfaces. The mass of the adsorbate is approximately proportional to the wavelength shift from the baseline within a narrow range of SPR wavelength. A 1-nm wavelength shift corresponds to ~150 pg/mm$^2$ of adsorbed protein for our SPR sensor operating at the wavelength of 750 nm (see Experimental Methods for details). The experimental values of surface coverage of Fg, Lyz, and BSA on four surfaces modified with different poly(β-peptoid) compositions as well as on bare gold are summarized in Table 3, which provides average values and standard deviations of three or more measurements. The chips were exposed to the protein solutions (1 mg/mL) in phosphate buffered saline (PBS) for 10 min.

TABLE 3

Protein Adsorption Measured by SPR spectroscopy.

| | Adsorbed mass (pg/mm$^2$) | | |
|---|---|---|---|
| entry | Fg | BSA | Lyz |
| PEtA20 | 4 (±4) | 0 (±3) | 7 (±14) |
| PEtA40 | 0 (±9) | 2 (±4) | 4 (±18) |
| PEtA80 | 10 (±10) | 13 (±16) | 18 (±5) |
| PMeA20 | −1 (±2) | 1 (±6) | 6 (±2) |
| Bare gold | 3697 (±618) | 1179 (±507) | 1204 (±419) |

All PMeA and PEtA surfaces demonstrate very low protein adsorption. In fact, the majority of the surface coverage values are below or close to the detection limit of SPR. Similar situations are encountered by PEG- or OEG-based materials. The reported values of Fg adsorption on PEG- or OEG-based materials detected by SPR range from a few to ten pg/mm$^2$, for example, 3.9±8.2 pg/mm$^2$ and 9±9 pg/mm$^2$ reported by two different groups. The reported values of Lyz adsorption on self-assembled OEG monolayer fall in the range of 3.5-17.5 pg/mm$^2$. Overall, the ability of PMeA and PEtA to resist protein adsorption is very similar to PEG.

The parity of PMeA and PEtA in their abilities to resist protein adsorption is interesting. The ethyl group ought to decrease the strength of hydration compared to the methyl group. The contact-angle data certainly confirm the difference in hydrophilicity of the surfaces grafted with PMeA and PEtA. The observation therefore demonstrates the absence of a simple correlation between the degree of hydrophilicity and protein resistance even among structurally closely related hydrophilic materials. Within the PEtA series, PEtA20 and PEtA40 display equivalent protein resistance, but PEtA80 shows a slight deterioration. One responsible suspect is a minute amount of amino repeat units might be present in PEtA80, as shown in the following chemical equation:

(3)

-continued

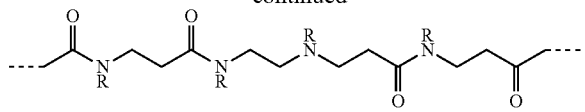

Although the amino repeat units have never been detected in the products of carbonylative polymerization of N-alkylaziridines, we have observed the amino defects in the product of carbonylative polymerization of unsubstituted aziridine. From a mechanistic viewpoint, the loss of selectivity occurs more readily when the concentration of the aziridine comonomer is high, as is the case when poly(β-peptoid)s with high molecular weights are synthesized. If this were the case, the surface would be positively charge at the neutral pH value of our experiment and therefore attract the negatively charged proteins and repel the positively charged proteins. Since the adsorption of the negatively charge BSA is no greater than those of the positively charged Lyz and Fg, the concern is perhaps gratuitous. Alternatively, the dependence of protein resistance on the molecular weight may stem from a higher minimum grafting density (defined as the number of repeat units per unit area) required for higher molecular weight polymers to display the same resistance to fouling as suggested by both theoretical and experimental studies on PEG. The present data reveal a somewhat higher adsorption of the smallest protein Lyz than Fg and BSA. This is consistent with the grafting density argument. In any event, the variations in the amount of adsorbed protein are of statistically marginal significance. Further investigation is necessary to draw any conclusion on the effects of molecular weight and grafting density.

Adsorption of Proteins in Blood Plasma and Serum.

Figure 7A:
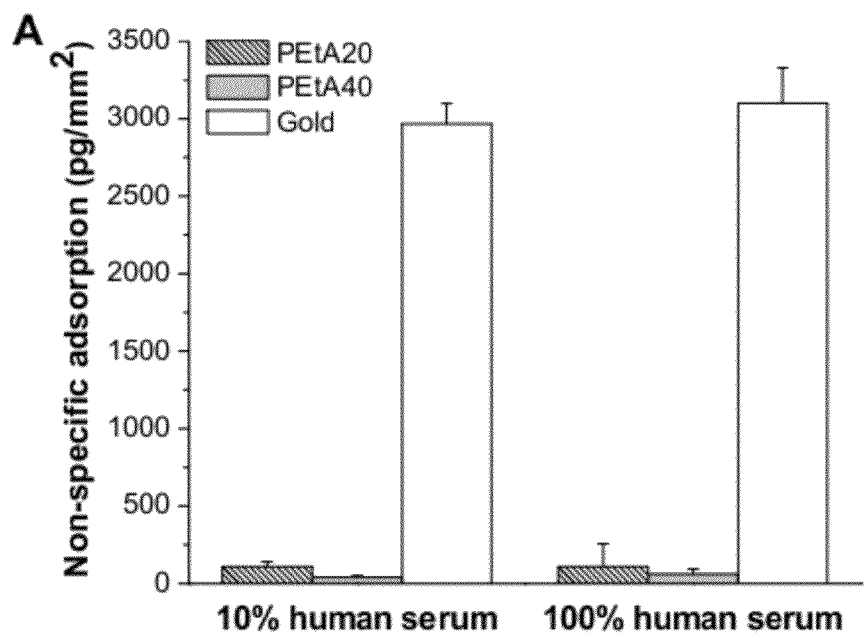
FIG. 7(a) provides SPR responses of PEtA20-grafted, PEtA40-grafted, and uncoated gold surfaces for nonspecific adsorption of 10% human serum in PBS and 100% human serum
Figure 7B:
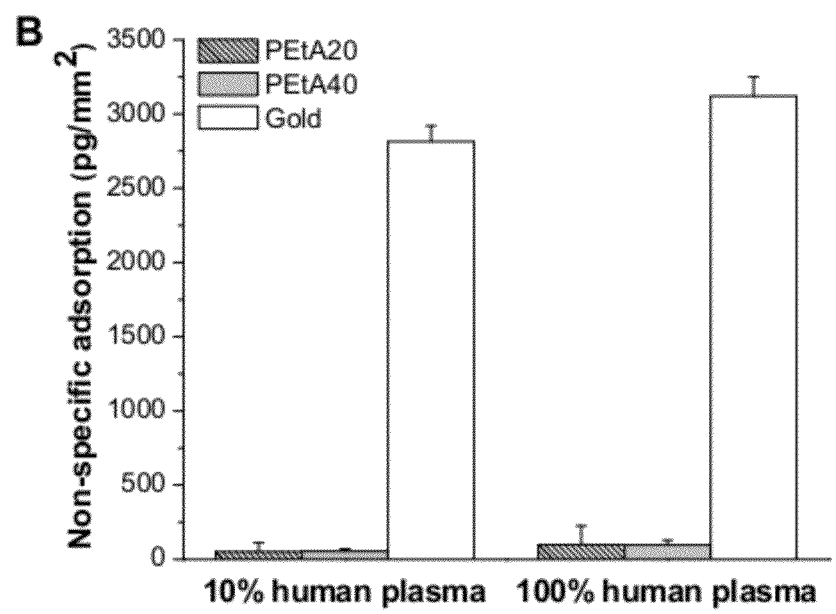
FIG. 7(b) shows the same for 10% human plasma in PBS and 100% human plasma, and the error bars represent the standard deviation of the mean.

The encouraging results of single protein adsorption prompted us to evaluate the antifouling property of representative members of the poly(β-peptoid)s in dilute and full human blood serum and plasma. We chose to test PEtA20 and PEtA40 because we were somewhat skeptical about the antifouling performance of the less hydrophilic PEtAs particularly in a more challenging environment and yet the wider synthetically achievable range of $X_n$ of PEtA than that of PMeA. As shown in FIG. 7, the PEtA20-functionalized surfaces allowed protein adsorption of 107 (±36), 108 (±148), 52 (±62), and 98 (±127) pg/mm² after the surfaces were exposed to 10% serum, 100% serum, 10% plasma, and 100% plasma for 10 min, respectively. The non-specific adsorption from 10% serum, 100% serum, 10% plasma, and 100% plasma onto the PEtA40-grafted surfaces were 39 (±12), 59 (±34), 57 (±15), and 97 (±32) pg/mm², respectively. The levels of protein adsorption on PEtA20 and PEtA40 surfaces are comparable to the adsorbed masses on PEG-based coating exposed to the same biological fluids under identical conditions. The experiments with serum and plasma thus convincingly corroborate the single protein experiments.

CONCLUSIONS

Two simple poly(β-peptoid)s with different degrees of polymerization are shown to be excellent surface materials for suppression of nonspecific protein adsorption. By extension, their copolymers (P(MeA-co-EtA) will also be excellent for such suppression. The resistance of these polymers to protein adsorption is comparable among themselves and to PEG as assessed by in situ SPR studies. The strong hydrogen-accepting ability of these poly(tertiary amide)s when forming hydrogen bonding with water is likely an important attribute to their excellent antifouling performance. The polymers are readily synthesized by catalytic carbonylative polymerization of the corresponding aziridines. The synthetic method is scalable and therefore makes the new type of antifouling polymers potentially useful for less expensive applications such as nonfouling membranes and marine and freshwater coatings in addition to the cost-tolerating biomedical applications such as implants, tissue engineering, and drug delivery.

What is claimed is:

1. A process for protecting a surface of an object from protein adsorption, the process comprising the steps of:
   binding a poly(β-peptoid) to the surface, the poly(β-peptoid) being selected from the group consisting of poly (N-methyl-β-alanine)s (PMeA) and poly(N-ethyl-β-alanine)s (PEtA) and polyl(methyl-β-alanine-co-ethyl-β-alanine) copolymers (P(MeA-co-EtA).

2. The process of claim 1, wherein the poly(β-peptoid) is PMeA.

3. The process of claim 1, wherein the poly(β-peptoid) is PEtA.

4. The process of claim 1, wherein the poly(β-peptoid) is P(MeA-co-EtA).

5. The process of claim 1, wherein the surface is a gold surface.

6. The process of claim 5, wherein the object is an electrode for a drug delivery microchip.

7. The process of claim 5, wherein in said step of binding, said poly(β-peptoid) includes a functional group X selected from a thiol group and dioxyphenylalanine.

8. The process of claim 7, wherein said functional group X is a thiol group such that the poly(β-peptoid) is a thiol-functionalized poly(β-peptoid), and, in said step of binding, the thiol-functionalized poly(β-peptoid) is bound to the gold surface by adsorption from solution, wherein a dilute solution of the thiol-functionalized poly(β-peptoid) is dissolved in a solvent and allowed to adsorb to the gold surface.

9. The process of claim 8, wherein the object is an electrode for a drug delivery microchip.

10. The process of claim 1, wherein the object is an object for placement in freshwater or saltwater.

11. The process of claim 1, further comprising the step of exposing the object to bodily fluids.

12. The process of claim 1, further comprising the step of exposing the object to freshwater or saltwater.

13. A medical implant coated with a poly(β-peptoid) selected from the group consisting of poly(N-methyl-β-alanine)s (PMeA) and poly(N-ethyl-β-alanine)s (PEtA) and polyl(methyl-β-alanine-co-ethyl-β-alanine) copolymers (P(MeA-co-EtA).

14. An object placed in freshwater or saltwater and having a surface in contact with the freshwater or saltwater, the surface being coated with a poly(β-peptoid) selected from the group consisting of poly(N-methyl-β-alanine)s (PMeA) and poly(N-ethyl-β-alanine)s (PEtA) and polyl(methyl-β-alanine-co-ethyl-β-alanine) copolymers (P(MeA-co-EtA).

15. A medical drug delivery device with a surface having a poly(β-peptoid) selected from the group consisting of poly (N-methyl-β-alanine)s (PMeA) and poly(N-ethyl-β-alanine)s (PEtA) and polyl(N-methyl-β-alanine-co-N-ethyl-β-alanine) copolymers (P(MeA-co-EtA).

* * * * *